(12) United States Patent
Geroni et al.

(10) Patent No.: US 6,593,303 B1
(45) Date of Patent: Jul. 15, 2003

(54) ANTI-TUMOR SYNERGETIC COMPOSITION

(75) Inventors: Cristina Geroni, Milan (IT); Marina Ripamonti, Milan (IT); Michele Caruso, Milan (IT); Antonino Suarato, Milan (IT)

(73) Assignee: Pharmacia & Upjohn, S.p.A., Milan (IT)

( * ) Notice: Subject to any disclaimer, the term of this patent is extended or adjusted under 35 U.S.C. 154(b) by 0 days.

(21) Appl. No.: 09/926,055

(22) PCT Filed: Jan. 31, 2000

(86) PCT No.: PCT/EP00/00746

§ 371 (c)(1), (2), (4) Date: Aug. 22, 2001

(87) PCT Pub. No.: WO00/50033

PCT Pub. Date: Aug. 31, 2000

(30) Foreign Application Priority Data

Feb. 25, 1999 (GB) ............................................... 9904386

(51) Int. Cl.⁷ .......................... A01N 43/04; A61K 31/70
(52) U.S. Cl. ............................ 514/34; 514/33; 514/449; 514/492
(58) Field of Search .............................. 514/6.4, 34, 6.3, 514/449, 492

(56) References Cited

U.S. PATENT DOCUMENTS

| | | |
|---|---|---|
| 4,177,263 A * | 12/1979 | Rosenberg et al. |
| 5,294,538 A | 3/1994 | Beach |
| 5,496,808 A | 3/1996 | Bargiotti et al. |
| 5,532,218 A | 7/1996 | Bargiotti et al. |
| 5,716,988 A * | 2/1998 | Ibrahim et al. |
| 5,919,816 A * | 7/1999 | Hausheer et al. |
| 6,080,877 A * | 6/2000 | Swindell et al. |
| 6,207,660 B1 * | 3/2001 | Sessler et al. |

OTHER PUBLICATIONS

Joseph Paul Eder, et al., Cancer Chemotherapy & Pharmacology, vol. 42, No. 4, pp. 327–335, "Sequence Effect of Irinotecan (CPT–11) and Topoisomerase II Inhibitors in Vivo", 1998.

Derwent Abstract, JP 2–157291, Jun. 18, 1990.

Derwent Abstract, JP 7–188034, Jul. 25, 1995.

\* cited by examiner

*Primary Examiner*—James O. Wilson
*Assistant Examiner*—Patrick Lewis
(74) *Attorney, Agent, or Firm*—MCDonnell Boehnen Hulbert & Berghoff

(57) ABSTRACT

There are provided the combined use of 4-demethoxy-3'-deamino-3'-aziridinyl-4'-methansulfonyl daunorubicin or 4-demethoxy-N,N-bis(2-chloroethyl)-4'-methansulfonyl daunorubicin and an anti-neoplastic anti-mitotic compound and/or a platinum derivative in the treatment of tumors, as well as in the prevention or treatment of metastasis or in the treatment of tumors by inhibition of angiogenesis.

41 Claims, No Drawings

ANTI-TUMOR SYNERGETIC COMPOSITION

This application is a 371 of PCT/EP00/00746 filed Jan. 31, 2000.

The present invention relates in general to the field of cancer treatment and, more particularly, provides an anti-tumor composition comprising an alkylating anthracycline and an anti-mitotic compound and/or a platinum derivative, having a synergistic or additive anti-neoplastic effect. The present invention provides, in a first aspect, a pharmaceutical composition for use in anti-neoplastic therapy in mammals, including humans, comprising an anthracycline of formula Ia or Ib

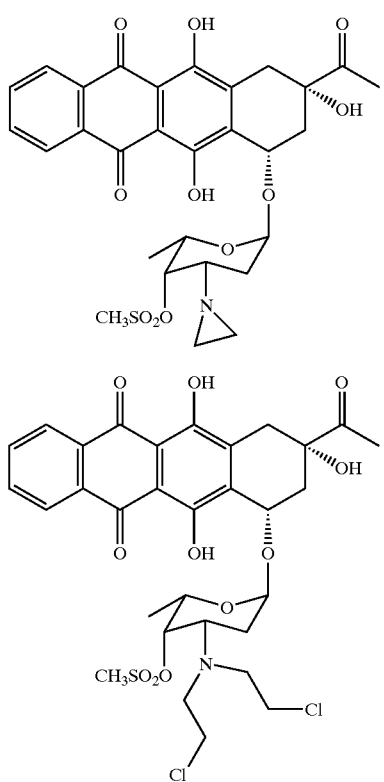

an anti-neoplastic anti-mitotic compound and/or a platinum derivative, and a pharmaceutically acceptable carrier or excipient.

The chemical names of the anthracyclines of formula Ia and Ib are 4-demethoxy-3'-deamino-3'-aziridinyl-4'-methansulfonyl daunorubicin (Ia) and 4-demethoxy-N,N-bis (2-chloroethyl)-4'-methansulfonyl daunorubicin (Ib). These anthracyclines were described in Anticancer Drug Design (1995), vol. 10, 641–653, and claimed respectively in U.S. Pat. No. 5,532,218 and U.S. Pat. No. 5,496,800. Both compounds intercalate into DNA via the chromophore and alkylate guanine at $N^-$ position in DNA minor groove via their reactive moiety on position 3' of the amino sugar. Compounds Ia and Ib are able to circumvent the resistance to all major classes of cytotoxics, indicating that the compounds represent a new class of cytotoxic anti-tumor drugs.

Anti-mitotic and platinum derivatives anti-neoplastic agents are described in various scientific publications. The main representatives of the anti-mitotic class are: Paclitaxel, Docetaxel, Vinblastine, Vincristine, Vindesine and Vinorelbine; see for example the review: Cancer, Principles and Practice of Oncology, Lippincott-Raven Ed. (1997), 467–483. Platinum derivatives used in clinical practice are: CisPlatin, Carboplatin, Oxaliplatin, Nedaplatin and Lobaplatin; see review Cancer, Principles and Practice of Oncology, Lippincott-Raven Ed. (1997), 418–432.

4-Demethoxy-3'-deamino-3'-aziridinyl-4'-methansulfonyl daunorubicin is the preferred compound to be used in the present invention, more preferably in combination with oxaliplatin docetaxel or paclitaxel. The present invention also provides a product comprising an anthracycline of formula Ia or Ib as defined above and an anti-neoplastic anti-mitotic compound and/or a platinum derivative, as combined preparation for simultaneous, separate or sequential use in antitumor therapy.

A further aspect of the present invention is to provide a method of treating a mammal including humans, suffering from a neoplastic disease state comprising administering to said mammal an anthracycline of formula Ia or Ib as defined above and an anti-neoplastic anti-mitotic compound and/or a platinum derivative, in amounts effective to produce a synergetic anti-neoplastic effect.

The present invention also provides a method for lowering the side effects caused by anti-neoplastic therapy with an anti-neoplastic agent in mammals, including humans, in need thereof, the method comprising administering to said mammal a combination preparation comprising an anti-neoplastic anti-mitotic compound and/or a platinum derivative as defined above and an anthracycline of formula Ia or Ib, as defined above, in amounts effective to produce a synergistic anti-neoplastic effect.

By the term "a synergistic anti-neoplastic effect" as used herein is meant the inhibition of the growth tumor, preferably the complete regression of the tumor, administering an effective amount of the combination of an anthracycline of formula Ia or Ib as defined above and an anti-mitotic compound and/or a platinum derivative to mammals, including human.

By the term "administered" or "administering" as used herein is meant parenteral and/or oral administration. By "parenteral" is meant intravenous, subcutaneous and intramuscolar administration. In the method of the subject invention, the anthracycline may be administered simultaneously with the compound with anti-mitotic activity, and/or a platinum derivative, or the compounds may be administered sequentially, in either order. It will be appreciated that the actual preferred method and order of administration will vary according to, inter alia, the particular formulation of the anthracycline of formula Ia or Ib being utilized, the particular formulation of the anti-mitotic compound, such as one of taxane analog class and of the platinum derivative being utilized, the particular tumor model being treated, and the particular host being treated In the method of the subject invention, for the administration of the anthracycline of formula Ia or Ib, the course of therapy generally employed is from about 0.1 to about 200 $mg/m^2$ of body surface area. More preferably, the course therapy employed is from about 1 to about 50 $mg/m^2$ of body surface area.

In the method of the subject invention, for the administration of the anti-mitotic compounds the course of therapy generally employed is from about 1 to about 1000 mg/m² of body surface area. More preferably, the course therapy employed is from about 10 to about 500 mg/m² of body surface area.

In the method of the subject invention, for the administration of the platinum derivative the course of therapy generally employed is from about 1 to about 1000 mg/m² of body surface area. More preferably, the course therapy employed is from about 100 to about 500 mg/m² of body surface area. The anti-neoplastic therapy of the present invention is in particular suitable for treating breast, ovary, lung, colon, kidney, stomach, pancreas, liver, melanoma, leukemia and brain tumors in mammals, including humans.

In a further aspect, the present invention is directed to the preparation of a pharmaceutical composition containing an effective amount of an anthracycline of formula Ia or Ib as defined above and an anti-neoplastic anti-mitotic compound and/or a platinum derivative in the prevention or treatment of metastasis or for the treatment of tumors by angiogenesis inhibition, as well as to the use of an anthracycline of formula Ia or Ib as defined above and an anti-neoplastic anti-mitotic compound and/or a platinum derivative for the treatment of tumors by angiogenesis inhibition or for the treatment or prevention of metastasis.

As stated above, the effect of an anthracycline of formula Ia or Ib and an anti-neoplastic anti-mitotic compounds, such as taxane derivatives, and/or a platinum derivative is significantly increased without a parallel increased toxicity. In other words, the combined therapy of the present invention enhances the antitumoral effects of the alkylating anthracycline and/or of the anti-mitotic compound and/or of the platinum derivative and thus yields the most effective and less toxic treatment for tumors. The superadditive actions of the combination preparation of the present invention are shown for instance by the following in vivo tests, which are intended to illustrate but not to limit the present invention.

Table 1 shows the antileukemic activity on disseminated L1210 murine leukemia obtained combining Ia with oxaliplatinum. At the dose of 8 mg/kg of oxaliplatinum alone (day +3) and at the dose of 1 mg/kg of Ia alone (day +1,2) were associated, without toxicity, with increase in life span (ILS %) values of 83 for both. Combining oxaliplatinum and Ia at the same doses with the same schedule an increase antitumor activity with ILS % value of 125 was observed, indicating a synergistic effect of the combination.

For these experiments Ia was solubilized in [Cremophor®/EtOH=6.5:3.5]/[normal saline]=20/80 v/v, while oxaliplatinum was solubilized in saline solution.

TABLE 1

Antileukemic activity against disseminated L1210[1] murine leukemia of Ia in combination with Oxaliplatinum

| Compound | Treatment schedule | Dose[2] (mg/kg/day) | ILS %[3] | Tox[4] |
|---|---|---|---|---|
| Ia | iv +1,2 | 1 | 83 | 0/10 |
| Oxaliplatinum | ip +3 | 8 | 83 | 0/10 |
| Ia + Oxaliplatinum | iv +1,2 ip +3 | 1 + 8 | 125 | 0/10 |

[1]) L1210 leukemia cells (10⁵/mouse) are injected iv on day 0.
[2]) Treatment is given starting on day 1 after tumor transplantation (day 0).
[3]) Increase in life span: [(median survival time of treated mice/median survival time of controls) × 100] − 100.
[4]) Number of toxic deaths/number of mice.

Table 2 shows the antitumor effect on subcutaneous implanted A549 human lung carcinoma obtained combining Ia with CisPlatin. At the doses of 3 mg/kg of CisPlatin alone (q4dx2) and at the dose of 1.5 mg/kg of Ia alone (q4dx3) were associated, without toxicity, with T.I. % values of 16 and 48, respectively. Combining CisPlatin and Ia, a significant increase in tumor growth delay was observed indicating a therapeutic advantage of the combination in comparison with the administration of the drug alone.

TABLE 2

Antitumor activity on A549 human lung carcinoma[1] of Ia in combination with CisPlatin.

| Compound | Treatment[2] schedule | Dose (mg/kg /day) | T.I. %[3] | Tox[4] | N° of Tumor-Free Survivors | T-C[5] N° of days | Body weight Reduction % (day) |
|---|---|---|---|---|---|---|---|
| Ia | iv q4dx3 | 1.5 | 48 | 0/9 | 0/9 | 5 | 9(14) |
| CisPlatin | iv q4dx2[6] | 3 | 16 | 0/9 | 0/9 | 0 | 2(18) |
| Ia + CisPlatin | iv q4dx3 + iv q4dx2[6] | 1.5 + 22 | 67 | 0/9 | 0/9 | 12 | 19(20) |

[1]) Tumor fragments are implanted s.c.
[2]) Treatment is given starting when the tumor is palpable.
[3]) Tumor inhibiton.
[4]) Number of toxic deaths/number of mice.
[5]) Tumor growth delay; T, median time to reach a tumor size of 1 g treated nude mice; C, median time to reach a tumor size of 1 g in control nude mice.
[6]) Treatment with CisPlatin started two days after treatment with Ia Table 3 shows the antitumor effect on subcutaneus implanted A549 human lung carcinoma obtained combining Ia with paclitaxel. At the doses of 22 and 33 mg/kg of paclitaxel alone(days +9,13,17) and at the dose of 2 mg/kg of Ia alone (days +7,11,15) were associated, without toxicity, with T.I. % values of 69,90 and 93, respectively. Combining paclitaxel and Ia, a significant increase in tumour growth delay was observed indicating a therapeutic advantage of the combination in comparison with the administration of the drug alone.

TABLE 3

Antitumor activity on A549 human lung carcinorma[1] of Ia in combination with paclitaxel.

| Compound | Treatment[2] schedule | Dose (mg/kg /day) | T.I. %[3] | Tox[4] | N° of Tumor-Free Survivors | T-C[5] N° of days | Body weight Reduction % (day) |
|---|---|---|---|---|---|---|---|
| Ia | iv +7,11,15 | 2 | 69 | 0/8 | 0/8 | 9 | 11 (13) |
| Paclitaxel | iv +9,13,17 | 22 | 90 | 0/8 | 0/8 | 27 | 0 |
|  |  | 33 | 93 | 0/8 | 0/8 | 29 | 0 |
| Ia + Pacitaxel | iv 7,11,15 + iv 9,13,17 | 2 + 22 | 93 | 1/8 | 0/8 | 35 | 18 (15) |
| Ia+ Paclitaxel | iv 7,11,15 + iv 9,13,17 | 2 + 33 | 90 | 0/6 | 0/6 | 40 | 23 (22) |

[1]) Tumor fragments are implanted s.c.
[2]) Treatment is given starting when the tumor is palpable.
[3]) Tumor inhibiton.
[4]) Number of toxic deaths/number of mice.
[5]) Tumor growth delay; T, median time to reach a tumor size of 1 g treated nude mice; C, median time to reach a tumor size of 1 g in control nude mice.

Table 4 shows the antitumor effect on subcutaneous implanted H207 human ovarian carcinoma obtained combining Ia with paclitaxel. At the doses of 22 and 33 mg/kg of paclitaxel alone (q4dx3)and at the dose of 1.5 mg/kg of Ia alone (q4dx3) were associated, without toxicity, with T.I. % values of 100,80 and 86, respectively. Combining paclitaxel and Ia, a significant increase in tumor growth delay and the appearance of the tumor free survivors (1/7 and 4/7) was observed indicating a therapeutic advantage of the combination in comparison with the administration of the drug alone.

Table 5 shows the antitumor effect on subcutaneous injected MX1 mammary carcinoma obtained combining Ia with docetaxel. At the doses of 5 and 10 mg/kg of docetaxel alone (q4dx3)and at the dose of 0.5 and 1 mg/kg of Ia alone (q4dx3) were associated, without toxicity, with T.I. % values of 60,99 and 46,94 respectively. Combining docetaxel and Ia, a significant increase in tumor growth delay and of the tumor free survivors (3/8, 5/8 and 7/8) was observed indicating a therapeutic advantage of the combination in comparison with the administration of the drug alone.

TABLE 4

Antitumor activity on H207 human ovarian carcinoma[1] of Ia in combination with paclitaxel.

| Compound | Treatment[2] schedule | Dose (mg/kg /day) | T.I. %[3] | Tox[4] | N° of Tumor-Free Survivors | T-C[5] N° of days | Body weight Reduction % (day) |
|---|---|---|---|---|---|---|---|
| Ia | iv q4dx3 | 1.5 | 100 | 0/7 | 0/7 | 47 | 7 (15) |
| Paclitaxel | iv q4dx3[6] | 22 | 80 | 0/7 | 0/7 | 9 | 0 |
|  |  | 33 | 86 | 0/7 | 0/7 | 12 | 3 (13) |
| Ia + Paclitaxel | iv q4dx3 + iv q4dx3[6] | 1.5 + 22 | 100 | 0/7 | 1/7 | >71 | 8 (20) |
| Ia+ Paclitaxel | iv q4dx3 + iv q4dx3[6] | 1.5 + 33 | 100 | 0/7 | 4/7 | >71 | 10 (16) |

[1]) Tumor fragments are implanted s.c.
[2]) Treatment is given starting when the tumor is palpable.
[3]) Tumor inhibiton.
[4]) Number of toxic deaths/number of mice.
[5]) Tumor growth delay; T, median time to reach a tumor size of 1 g treated nude mice; C, median time to reach a tumor size of 1 g in control nude mice.
[6]) Treatment with paclitaxel started two days after treatment with Ia

TABLE 5

Antitumor activity on MX1 mammary carcinoma[1] of Ia in combination with paclitaxel.

| Compound | Treatment[2] schedule | Dose (mg/kg/day) | T.I. %[3] | Tox[4] | N° of Tumor-Free Survivors | TGD[5] (lg) days | Body weight Reduction % (day) |
|---|---|---|---|---|---|---|---|
| Ia | iv 8,12,16 | 0.5 | 46 | 0/8 | 0/8 | 1 | 0 |
|  |  | 1 | 94 | 0/7 | 1/7 | 2 | 5 (17) |
| Taxotere | iv 10,14,18 | 5 | 60 | 0/8 | 0/8 | 1 | 0 |
|  |  | 10 | 99 | 0/8 | 2/8 | 42 | 8 (25) |
| Ia | iv 8,12,16 | 0.5 + 5 | 95 | 0/8 | 3/8 | 2 | 6 (17) |
| Taxotere | iv 10,14,18 | 0.5 + 10 | 96 | 0/8 | 5/8 | >78 | 11 (17) |
|  |  | 1 + 5 | 98 | 0/8 | 7/8 | >78 | 10 (17) |
|  |  | 1 + 10 | 98 | 3/8 | 5/8 | >78 | 15 (18) |

[1]) Tumor fragments were injected s.c.
[2]) Treatment is given starting when the tumor is palpable.
[3]) Tumor inhibiton.
[4]) Number of toxic deaths/number of mice.
[5]) TGD: Tumor growth delay treated - Tumor growth delay control

What is claimed is:

1. A composition suitable for treating tumors, comprising:
(1) an anthracycline of formula Ia or Ib:

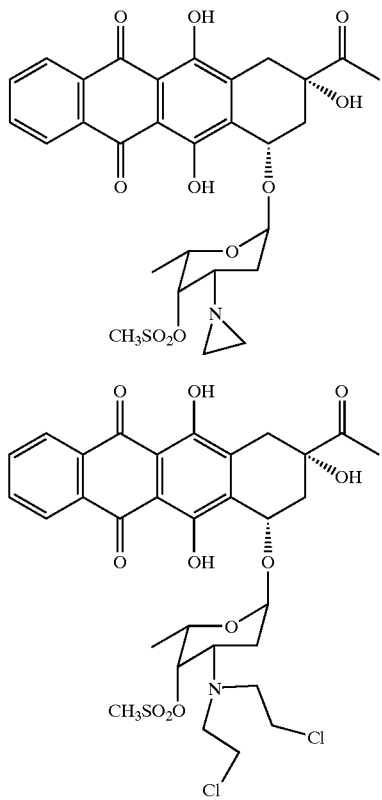

and
(2) an antineoplastic anti-mitotic compound and/or a platinum derivative.

2. The composition of claim 1, which contains the anthracycline of formula Ia.

3. The composition of claim 1, which contains the anthracycline of formula Ib.

4. The composition of claim 1, which contains the antineoplastic anti-mitotic compound.

5. The composition of claim 1, which contains the platinum derivative.

6. The composition of claim 1, which contains the antineoplastic anti-mitotic compound and the platinum derivative.

7. The composition of claim 1, wherein the anthracycline is 4-demethoxy-3'-deamino-3'-aziridinyl-4'-methansulfonyl daunorubicin.

8. The composition of claim 1, wherein the anti-mitotic compound is paclitaxel or docetaxel.

9. The composition of claim 1, wherein the platinum derivative is oxaliplatin.

10. The composition of claim 1, which contains 4-demethoxy-3'-deamino-3'-aziridinyl-4'-methansulfonyl daunorubicin.

11. The composition of claim 1, which comprises a synergistic amounts of (1) and (2).

12. The composition of claim 1, wherein the platinum derivative is cis-platin.

13. A method of treating a mammal for tumors, comprising administering to the mammal an effective amount of the composition of claim 1.

14. The method of claim 13, wherein the mammal is a human.

15. The method as claimed in claim 13, wherein the anthracycline is 4-demethoxy-3'-deamino-3'-aziridinyl-4'-methansulfonyl daunorubicin.

16. A method of treating metastasis in a mammal, comprising administering an effective amount of the composition claimed in claim 1 to the mammal.

17. The method of claim 16, wherein the mammal is a human.

18. A method of treating a tumor in a mammal by inhibiting angiogenesis, comprising administering an effective amount of the composition claimed in claim 1 to the mammal.

19. The method of claim 18, wherein the mammal is a human.

20. A method of treating a mammal for tumors, comprising administering to the mammal an effective amount of:

(1) an anthracycline of formula Ia or Ib:

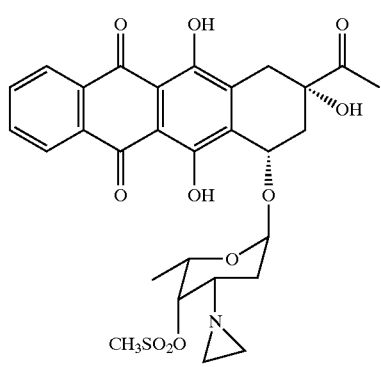

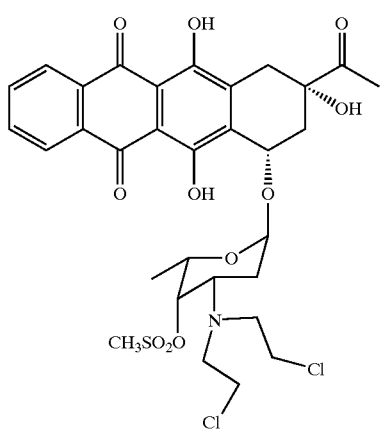

and (2) an antineoplastic anti-mitotic compound and/or a platinum derivative.

21. The method of claim 20, wherein the anthracycline of formula Ia is administered.

22. The method of claim 20, wherein the anthracycline is administered.

23. The method of claim 20, wherein the antineoplastic anti-mitotic compound is administered.

24. The method of claim 20, wherein the platinum derivative is administered.

25. The method of claim 20, wherein the antineoplastic anti-mitotic compound and the platinum derivative are administered.

26. The method of claim 20, wherein the anthracycline is 4-demethoxy-3'-deamino-3'-aziridinyl-4'-methansulfonyl daunorubicin.

27. The method of claim 20, wherein the anti-mitotic compound is paclitaxel or docetaxel.

28. The method of claim 20, wherein the platinum derivative is oxaliplatin.

29. The method of claim 20, wherein the platinum derivative is cis-platin.

30. The method of claim 20, wherein the mammal is a human.

31. A method of treating metastasis in a mammal, comprising administering to the mammal an effective amount of:

(1) an anthracycline of formula Ia or Ib:

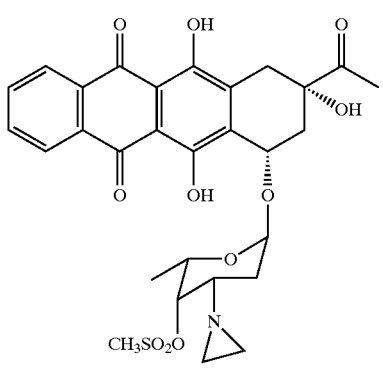

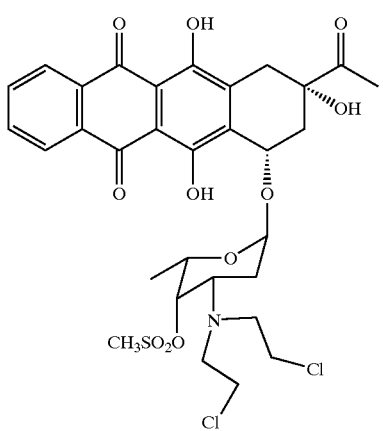

and (2) an antineoplastic anti-mitotic compound and/or a platinum derivative.

32. The method of claim 31, wherein the anthracycline of formula Ia is administered.

33. The method of claim 31, wherein the anthracycline is administered.

34. The method of claim 31, wherein the antineoplastic anti-mitotic compound is administered.

35. The method of claim 31, wherein the platinum derivative is administered.

36. The method of claim 31, wherein the antineoplastic anti-mitotic compound and the platinum derivative are administered.

37. The method of claim 31, wherein the anthracycline is 4-demethoxy-3'-deamino-3'-aziridinyl-4'-methansulfonyl daunorubicin.

38. The method of claim 31, wherein the anti-mitotic compound is paclitaxel or docetaxel.

39. The method of claim 31, wherein the platinum derivative is oxaliplatin.

40. The method of claim 31, wherein the platinum derivative is cis-platin.

41. The method of claim 31, wherein the mammal is a human.

\* \* \* \* \*